(12) United States Patent
Fujita et al.

(10) Patent No.: US 7,367,940 B2
(45) Date of Patent: May 6, 2008

(54) CAPSULAR MEDICAL APPARATUS

(75) Inventors: Manabu Fujita, Hino (JP); Akio Uchiyama, Yokohama (JP)

(73) Assignee: Olympus Corporation, Tokyo (JP)

( * ) Notice: Subject to any disclaimer, the term of this patent is extended or adjusted under 35 U.S.C. 154(b) by 460 days.

(21) Appl. No.: 10/846,970

(22) Filed: May 14, 2004

(65) Prior Publication Data

US 2005/0038321 A1 Feb. 17, 2005

(30) Foreign Application Priority Data

May 14, 2003 (JP) .............................. 2003-136395

(51) Int. Cl.
*A61B 1/04* (2006.01)
(52) U.S. Cl. ..................... 600/118; 600/109; 600/160
(58) Field of Classification Search ................ 600/117, 600/118, 160, 109; 348/74, 75, 76
See application file for complete search history.

(56) References Cited

U.S. PATENT DOCUMENTS

| | | | |
|---|---|---|---|
| 5,604,531 A | | 2/1997 | Iddan et al. |
| 6,005,613 A | * | 12/1999 | Endsley et al. .......... 348/231.6 |
| 6,012,103 A | * | 1/2000 | Sartore et al. ................. 710/8 |
| 6,101,076 A | * | 8/2000 | Tsai et al. .................... 361/90 |
| 6,105,097 A | * | 8/2000 | Larky et al. ................. 710/314 |
| 6,106,457 A | * | 8/2000 | Perkins et al. .............. 600/175 |
| 6,460,143 B1 | * | 10/2002 | Howard et al. ............. 713/323 |
| 6,467,042 B1 | * | 10/2002 | Wright et al. ............... 713/320 |
| 6,638,212 B1 | * | 10/2003 | Oshima ...................... 600/109 |
| 6,662,301 B1 | * | 12/2003 | Sekine et al. ............... 713/320 |
| 2002/0184122 A1 | * | 12/2002 | Yamaguchi et al. .......... 705/30 |
| 2003/0023150 A1 | * | 1/2003 | Yokoi et al. ................. 600/300 |
| 2003/0097042 A1 | * | 5/2003 | Eino ........................... 600/118 |
| 2004/0019255 A1 | * | 1/2004 | Sakiyama ................... 600/175 |

FOREIGN PATENT DOCUMENTS

| | | |
|---|---|---|
| EP | 0 667 115 A1 | 8/1995 |
| JP | 2001-203789 | 7/2001 |

* cited by examiner

*Primary Examiner*—John P. Leubecker
(74) *Attorney, Agent, or Firm*—Scully, Scott, Murphy & Presser, P.C.

(57) ABSTRACT

A capsular medical apparatus according to the present invention includes a capsule which can be swallowed or inserted in the body, a recording device which receives living body information transmitted from the capsule and which records the received information, and a display device of the living body information. Further, the capsular medical apparatus includes a USB connector which connects and disconnects the recording device and the display device, a voltage detecting circuit which detects the connection between the recording device and the display device, and a USB cable which transmits the living body information to the display device from the recording device.

23 Claims, 8 Drawing Sheets

CAPSULAR MEDICAL APPARATUS

This application is based upon and claims the benefit of priority from the prior Japanese Patent Application No. 2003-136395 filed on May 14, 2003; the entire contents of which are incorporated herein by reference.

BACKGROUND OF THE INVENTION

1. Field of the Invention

The present invention relates to a capsular medical apparatus for obtaining living body information.

2. Description of the Related Art

Recently, there is a capsular medical apparatus which easily examines the body by the capsule shape that facilitates the swallowing of a patient.

For example, U.S. Pat. No. 5,604,531 discloses a potable storage unit and a stationary storage unit.

SUMMARY OF THE INVENTION

According to the present invention, a capsular medical apparatus comprises a capsule which can be swallowed or inserted in the body, a recording device which receives living body information transmitted from the capsule and which records the received information, and a display device of the living body information. The capsular medical apparatus further comprises attaching/detaching means which connects and disconnects the recording device and the display device, detecting means which detects the connection between the recording device and the display device, and transfer means which transfers the living body information to the display device from the recording device. The operation or the like is checked by connecting the display device upon starting the apparatus or the like. When the operation check or the like is unnecessary, the display device is detached and thus the load of the patient is reduced.

The above and other objects, features and advantages of the invention will become more clearly understood from the following description referring to the accompanying drawings.

BRIEF DESCRIPTION OF THE DRAWINGS

FIGS. 1 to 7 relate to a first embodiment of the present invention, FIG. 1 is a diagram showing the structure of a capsular medical apparatus, FIG. 2 is a flowchart showing the flow for adding time information to image data received by a recording device and recording the information, FIG. 3 is a diagram showing an image format additionally having a time stamp on the received image, FIG. 4 is a diagram showing a display example of the image additionally having the time stamp on the display device, FIG. 5 is a diagram showing a display example of an image including contents of parameter setting upon displaying the receiving strength at a designated time interval, FIG. 6 is a diagram showing a display example of an image for corresponding examination by clicking a tab in a state in which a plurality of examinations are opened, FIG. 7 is a diagram showing a display example of an image displayed at the corresponding piece interval by selecting the number of divisions.

DESCRIPTION OF THE PREFERRED EMBODIMENTS

A first embodiment of the present invention will be described with reference to FIGS. 1 to 7.

Figure 1:
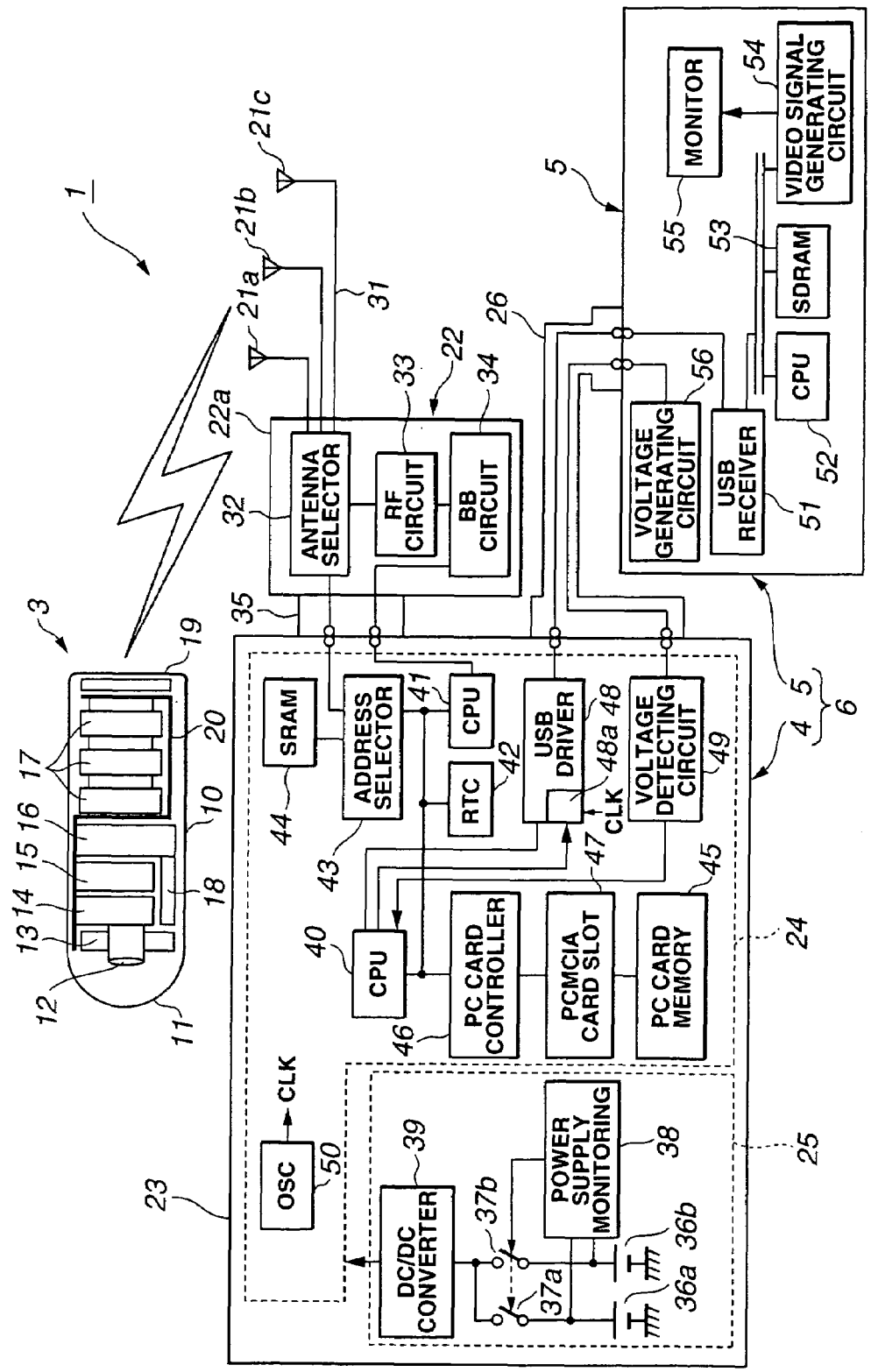

Referring to FIG. 1, a capsular medical apparatus 1 according to the first embodiment of the present invention comprises: a capsular in-body unit 3 which is inserted in the body by swallowing or inserting operation or the like and which picks up an image (hereinafter, abbreviated to a capsule); a recording device 4 which is arranged outside the body and receives, by radio waves, living body information transmitted from a capsule 3 and which records the data; and a display device 5 which is connected detachably (attached and detached) to the recording device 4 and which displays the living body information. The recording device 4 and the display device 5 form an extracorporeal device 6.

The recording device 4 has small size and light weight for recording (storing) image data transmitted from the capsule 3 so as to be attached to a white cloth or jacket of a patient. Upon displaying the image so as to check the operation or the like, the recording device 4 is connected to the display device 5 having a function for displaying the image on the recording device 4 by a USB cable 26.

In the capsule 3, at one end portion (front end) in an accommodating container 10 that is capsule-shaped and is sealed, an illuminating and observing window 11 that is semi-spherical and contains a transparent member is formed. Further, in the capsule 3, an objective optical system 12 is attached to a lens frame facing the center portion of the illuminating and observing window 11, and four white LEDs 13 or the like are respectively arranged as light emitting elements forming illuminating means at four positions or the like around the objective optical system 12.

A CMOS sensor 14 or the like is arranged, as an image sensor for obtaining image information on the living body, at the position for forming images in the objective optical system 12. The CMOS sensor 14 comprises, on the back surface side, a signal processing circuit 15 which generates the image data (e.g., JPEG data) that is obtained by performing the signal processing of the CMOS sensor 14 and compressing the processed data; a communication circuit 16 for radio communication; and a plurality of button batteries 17 which feed the power for operation to the CMOS sensor 14 and the signal processing circuit 15.

Further, at the side portion adjacent to the CMOS sensor 14, an antenna 18, which is connected to the communication circuit 16 and which irradiates and receives the electric waves for radio communication with (antennas 21a to 21c) of the extracorporeal recording device 4, is provided. Also at the rear end adjacent to the plurality of button batteries 17, a switch 19, which performs the on/off operation of the power supply, is provided. The CMOS sensor 14, the signal processing circuit 15, and the communication circuit 16 are electrically connected by a flexible substrate 20. Further, the flexible substrate 20 is connected to the plurality of button batteries 17 via the switch 19.

On the other hand, the extracorporeal recording device 4 comprises: an antenna unit 22 to which the plurality of antennas 21a to 21c are connected; a recording processing block 24 that is accommodated in a casing 23 to which the antenna unit 22 is detachably connected and that records image data; and a power supply block 25 which supplies power to the recording processing block 24 and the like.

The recording device 4 is detachably connected to the display device 5 by the USB cable 26 (as data transfer means for transferring data to the display device 5 from the recording device 4). By connecting the display device 5 to the recording device 4 via the USB cable 26, the image received by the recording device 4 and the image stored in the recording device 4 are transferred to the display device 5 side. The display device 5 performs the decompressing processing of the transferred image data, displays the processed data on the display screen, and simultaneously edits and displays a plurality of images.

In addition to one terminal on the recording device 4 side in the USB cable 26 and the other terminal on the display device 5, a conductive terminal is provided. The USB cable 26 is freely detachably connected to the conductive terminal of the USB connector of the recording device 4 and the conductive terminal of the USB connector of the display device 5.

The antenna unit 22 has an exterior case containing a resin casing 22a whose inner or external surface is subjected to the shielding processing such as metal plating. The antenna unit 22 comprises: an antenna selector 32 which switches the antennas 21a to 21c connected thereto by a coaxial cable 31; a high-frequency circuit (abbreviated to an RF circuit) 33 which communicates data by radio waves and which is connected to the antennas 21a to 21c via the antenna selector 32; a base band circuit (abbreviated to a BB circuit) 34 which generates the base band signal that is demodulated by the RF circuit 33; and a connector 35 which is detachably connected to the recording device 4.

A portion for handing the high-frequency signal, mainly including the RF circuit 33, is sealed in the antenna unit 22. A connecting portion to the recording device 4 in the connector 35 handles only the base band signal (and antenna switching signal). Thus, the reliability and the stability of the operation are improved.

The casing 23 of the recording device 4 is made of metal or (shielding processed) resin, and accommodates a power supply block 25 and a recording processing block 24.

The power supply block 25 comprises: batteries 36a and 36b arranged in parallel therewith; switches 37a and 37b which are serially connected to the batteries 36a and 36b; a power supply monitoring circuit 38 which monitors voltages of the batteries 36a and 36b and enables one of the switches 37a and 37b; and a DC/DC converter 39 which is connected to the ON-operation battery and converts the voltage into DC power of a voltage value necessary for the recording processing block 24.

The DC current of the DC/DC converter 39 is supplied to the antenna unit 22 side via the connector 35 as well as the recording processing block 24.

The recording processing block 24 comprises: a CPU 40 which controls the recording device 4; a CPU 41 which mainly controls the antenna unit 22; a real-time clock (abbreviated to an RTC) which is connected to both the CPUs 40 and 41, manages the time, and outputs information on the date upon receiving the image; an address selector 43 which is connected to both the CPUs 40 and 41 and is connected to the antenna selector 32; a memory (SRAM) 44 which is connected to the address selector 43 and temporarily stores data from the selected antenna selector 32; a PC card controller 46 which is connected to both the CPUs 40 and 41 and controls the operation for writing the data to a PC card memory 45; a PCMCIA slot 47 which is connected to the PC card controller 46; the PC card memory 45 which is detachably connected to the PCMCIA slot 47 and stores received and demodulated image data (JPEG data); a USB driver 48 which performs the processing for transferring data to the display device 5 via the USB cable 26 when the display device 5 is connected to the recording device 4 via the USB cable 26; a voltage detecting circuit 49, (as detecting means which detects the connection between the recording device 4 and the display device 5), which detects the connection to the display device 5 by using the voltage; and an oscillator (OSC) 50 which supplies reference clocks to the CPU 41 and the like.

The CPU 40 determines whether or not it is connected to the display device 5 based on the level of (the signal of) the voltage of the voltage detecting circuit 49. The CPU 40 transmits a control signal for opening or closing a gate to a clock gate 48a provided for the USB driver 48, and controls the operation of the USB driver 48.

That is, in a state in which a predetermined voltage is detected and the display device 5 is connected to the CUP 40, the clock gate 48a is opened, thus to supply a clock CLK to the USB driver 48. Further, the USB driver 48 is set to the operating state. Then, the CPU 40 records the image data received by the antenna unit 22 to the PC card memory 45 and transmits the recorded-data to the display device 5 side via the USB driver 48.

In a state in which the predetermined voltage is not detected and the display device 5 is not connected to the CPU 40, the CPU 40 closes the clock gate 48a and sets a standby mode in which the clock CLK is not supplied to the USB driver 48 and controls the operation for reducing the power consumption by the USB driver 48. In this case, the CPU 40 records the data received by the antenna unit 22 to the PC card memory 45.

As mentioned above, according to the first embodiment, the recording device 4 and the display device 5 are independently formed and the recording device 4 is detachable to the display device 5 by the USB cable 26 as transfer means for transferring the data. Thus, only the recording device 4 is used to handle the capsule 3. Further, the capsule 3 is used by connecting the recording device 4 and the display device 5. Consequently, the load of the patient is reduced and the operability is ensured. Further, the recording device 4 is operated in different operating modes depending on the presence or absence of the connection at the USB cable 26.

Figure 3:
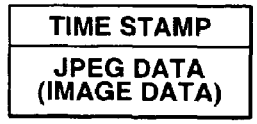

Each time when the antenna unit 22 receives the image data from the capsule 3, the CPU 40 or CPU 41 reads time data from the RTC 42, adds the time data to the received image data (specifically, JPEG data), and stores the image data with a time stamp in the PC card memory 45. FIG. 3 shows an image format additionally having the time data with the image data.

The display device 5 comprises: a USB receiver 51 which is connected to the USB driver 48 in the recording device 4 by the USB cable 26, and receives the JPEG data as the image data transmitted from the USB driver 48; a CPU 52 which is connected to the USB receiver 51 via a bus and controls the operation of the display device 5 and performs the decompression processing of the image data; a memory (specifically, SDRAM) 53 which is connected to the bus, temporarily stores the image data, and is used as a work area of the CPU 52; a video signal generating circuit 54 which is connected to the bus, and performs the processing for converting a video signal (e.g., RGB video signal) for displaying the image of the image data subjected to the decompression processing by the CPU 52; a monitor 55 which is connected to an output terminal of the video signal generating circuit 54 and displays the corresponding image by inputting the RGB video signal or the like as the video signal; and a voltage generating circuit 56 which generates the voltage for detecting whether or not the recording device 4 is connected by connecting one terminal of the voltage generating circuit 56 to the USB cable 26.

Figure 4:
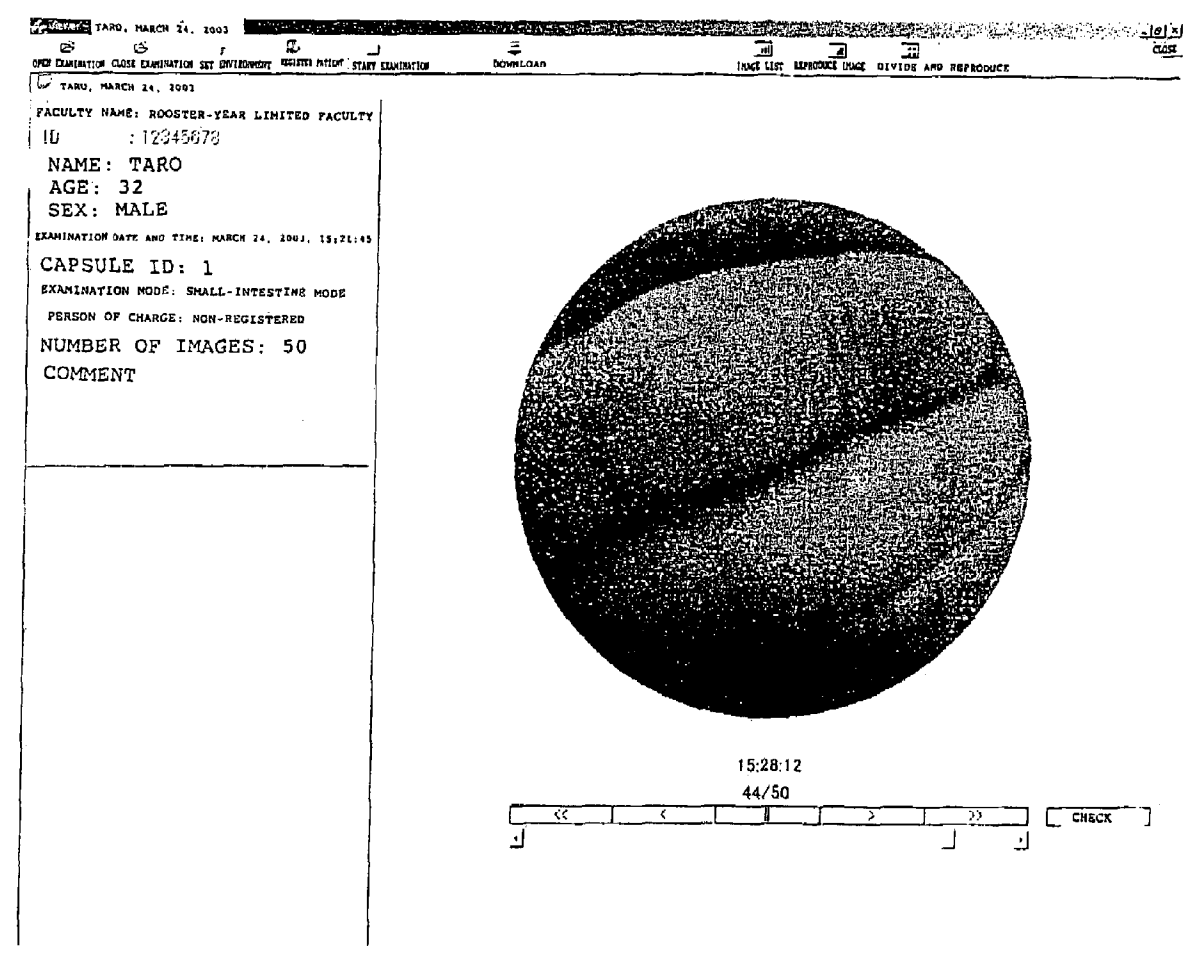

As mentioned above, when the display device 5 is connected to the recording device 4 by the USB cable 26, the recording device 4 transmits, to the display device 5, the image data with the time stamp additionally having the time data. The display device 5 decompresses the JPEG data and displays the received time at the portion on the bottom of the image as shown in FIG. 4.

As mentioned above, according to the first embodiment, the recording device 4 stores, in the PC card memory 45, the image data transmitted from the capsule 3 as the image data with the time stamp additionally having the received time.

Further, according to the first embodiment, the display device 5 is detachable to the recording device 4, and the recording device 4 detects whether or not the display device 5 is connected thereto. When the display device 5 is connected to the recording device 4, the image data with the time stamp is stored in the PC card memory 45 and is transmitted to the display device 5, thus to check in realtime the image by displaying the image on the monitor 55 of the display device 5.

When the image does not need to be checked, the USB cable 26 is detached from the recording device 4, and thus the recording device 4 is detached from the display device 5. The USB cable 26 for connection to the display device 5 is not connected to the recording device 4 and therefore the load of the patient is reduced. The operability (easy use) is improved.

Next, the typical operation will be described with reference to FIG. 2 according to the first embodiment.

Upon examining the body by using the capsule 3, when the operation of the capsule 3 is checked, the recording device 4 is connected to the display device 5 by the USB cable 26 as shown in FIG. 1, and the power of the recording device 4 and the display device 5 is turned on as shown in step S1 in FIG. 1, and the power of the capsule 3 is turned on. In this case, the recording device 4 is attached to a white cloth or the like of the patient.

Then, in step S2, the CPU 40 of the recording device 4 determines whether or not the display device 5 is connected to the CPU 40 (by the voltage detecting signal from the voltage detecting circuit 49). If the CPU 40 determines that the display device 5 is connected to the recording device 4, in step S3, the CPU 40 opens the clock gate 48a of the USB driver 48, and the clock CLK is supplied to the USB driver 48 to (reset the standby state) and set the operating state.

In step S4, when the CPU 40 receives the image data transmitted from the capsule 3, the CPU 40 adds the time data of the RTC 42 to the image data so as to form the image data additionally having the time stamp (as shown in FIG. 3) and stores the image data in the PC card memory 45 in the recording device 4. Further, the CPU 40 transmits the image data additionally having the time stamp to the display device 5 via the USB cable 26.

In step S5, the display device 5 displays the image to which the receiving time is superimposed.

Specifically, the display device 5 compresses the image additionally having the transmitted time stamp, therefore, the CPU 52 in the display device 5 decompresses the data, and temporarily stores the decompressed data in the memory (SDRAM) 53. The video signal generating circuit 54 transmits the decompressed image data, converts the image data into the video signal, and displays the image with the superimposed receiving time on the display screen of the monitor 55 as shown in FIG. 4.

The processing sequence returns to step S2. By connecting the display device 5 to the recording device 4, the medical staff can check the picked-up image by the capsule 3 in realtime, and can know the obtaining time of the image.

After that, the patient swallows the capsule 3 and the medical staff can check the image picked-up by the capsule 3 in this state and can know the obtaining time of the time. When the image does not need to be monitored, the USB cable 26 is detached from the recording device 4 and the load of the patient is reduced.

In this case, when the CPU 40 of the recording device 4 determines in step S2 that the display device 5 is not connected, in step S6, the CPU 40 closes the clock gate 48a of the USB driver 48 and the standby mode is set to prevent the clock CLK from being supplied to the USB driver 48.

In step S7, the CPU 40 receives the image data (specifically, JEPG data) transmitted from the capsule 3. Then, the CPU 40 adds the time data of the RTC 42 to the image data, set the image data additionally having the time stamp (as shown in FIG. 3), and stores the image data to the PC card memory 45 in the recording device 4. The processing sequence returns to step S2.

When the operation of the capsule 3, recording device 4, and display device 5 is checked after swallowing the capsule 3 by the patient, the USB cable 26 is not connected to the patient by detaching, from the recording device 4, the USB cable 26 for connecting the recording device 4 and the display device 5 and therefore the load of the patient is reduced. In this state, the image data picked-up by the recording device 4 is stored.

According to the first embodiment, as processed above, when the operation is being checked, the recording device 4 is connected to the display device 5 by the USB cable 26. Thus, the receiving time is added to the image data from the capsule 3 received by the recording device 4 and is stored. Further, the image is displayed in realtime on the monitor 55 of the display device 5.

When the image does not need to be checked on the monitor 55, the necessary image data is stored by using only the recording device 4 by detaching the USB cable 26 and the display function is not provided. Therefore, the convenience is preferable for the patient without increasing the scale.

By detaching the USB cable 26, the USB driver 48 is set to the standby mode and therefore the energy consumption is reduced.

Therefore, the first embodiment has the following advantages.

That is, the recording device 4 is reduced in size and the living body information transmitted from the capsule 3 is checked by the display device 5 as needed without failing to record the information. It is easily checked at the arbitrary time during the examination whether or not the normal operation is possible.

According to the first embodiment, the receiving strength is detected by the recording device 4 and the antennas 21a to 21c with the high receiving-strength are switched so as to receive the signals from the capsule 3.

The receiving strengths of the capsule 3 and the recording device 4 are displayed at the designated time interval (when the display device 5 is connected). In this case, the capsule 3 and the recording device 4 control the gain based on the value of the detected receiving strength.

Under the gain control, a predetermined receiving strength is ensured to receive and transmit the signal by the antenna. If the proper receiving state is not set under the gain control, the antennas are switched so as to use the antenna for properly receiving the signal.

Figure 5:
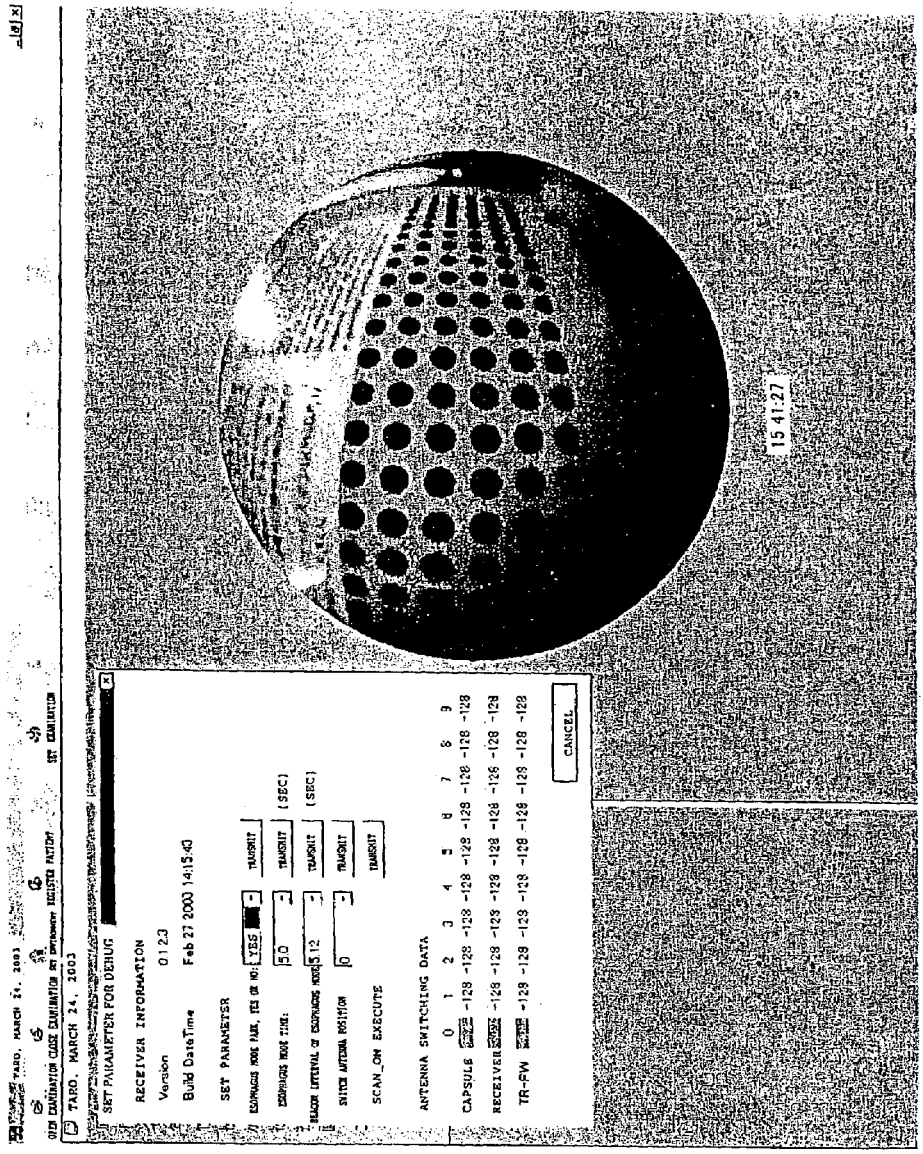

FIG. 5 shows a state in which the recording device 4 (receiver in FIG. 5) receives the signal from the capsule 3 via an antenna (e.g., antenna 21a in FIG. 1) having antenna switching data 0. Referring to FIG. 5, the antennas are switched by using antenna switching 0 to 9.

Figure 6:
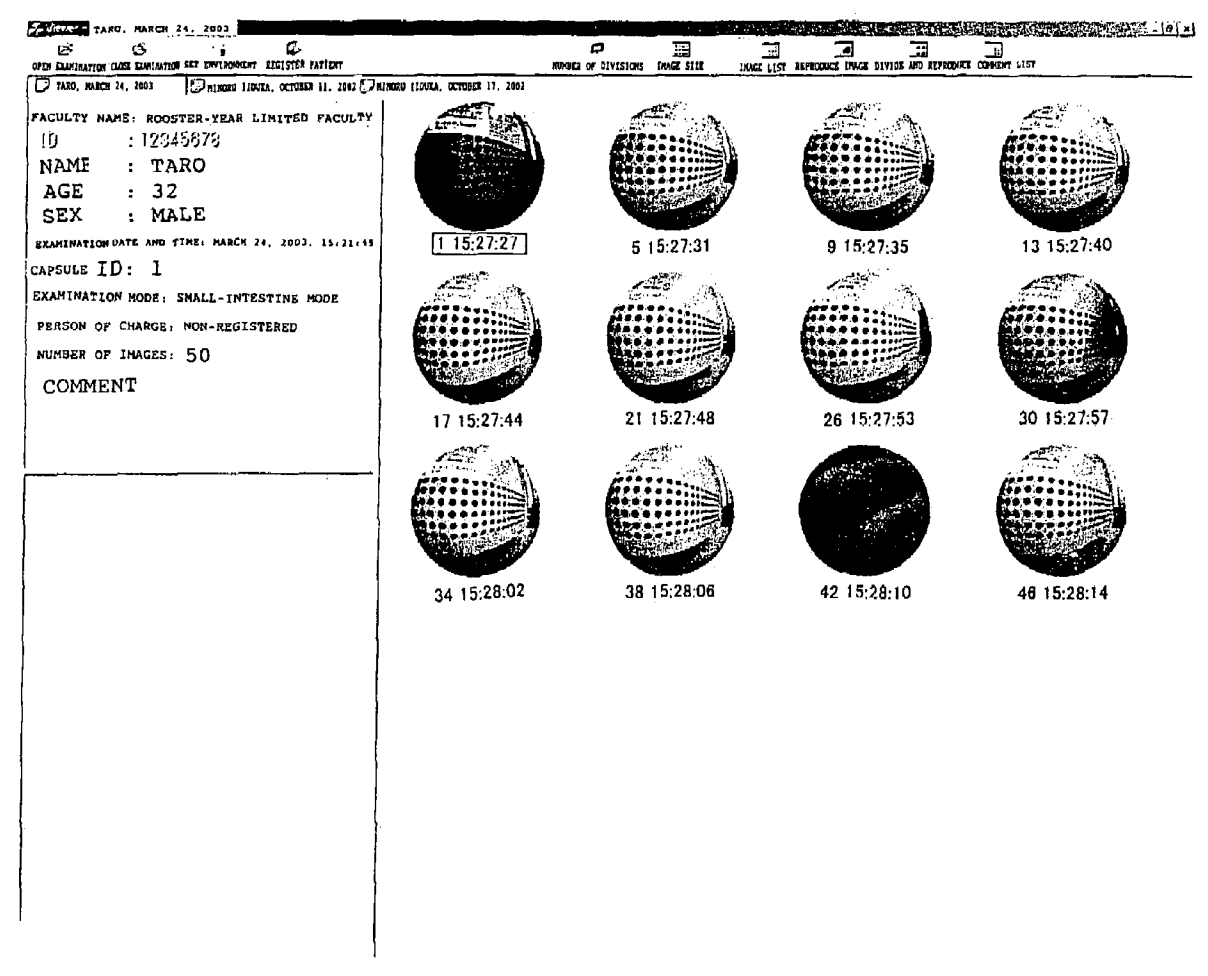

According to the first embodiment, referring to FIG. 6, a plurality of examinations (specifically, Taro and Minoru Iiduka) are opened in the display device 5 and a tab is clicked, thereby displaying the corresponding image for examination on the display screen of the monitor as a thumbnail image. In this case, the receiving time is displayed on the bottom of the images.

Figure 7:
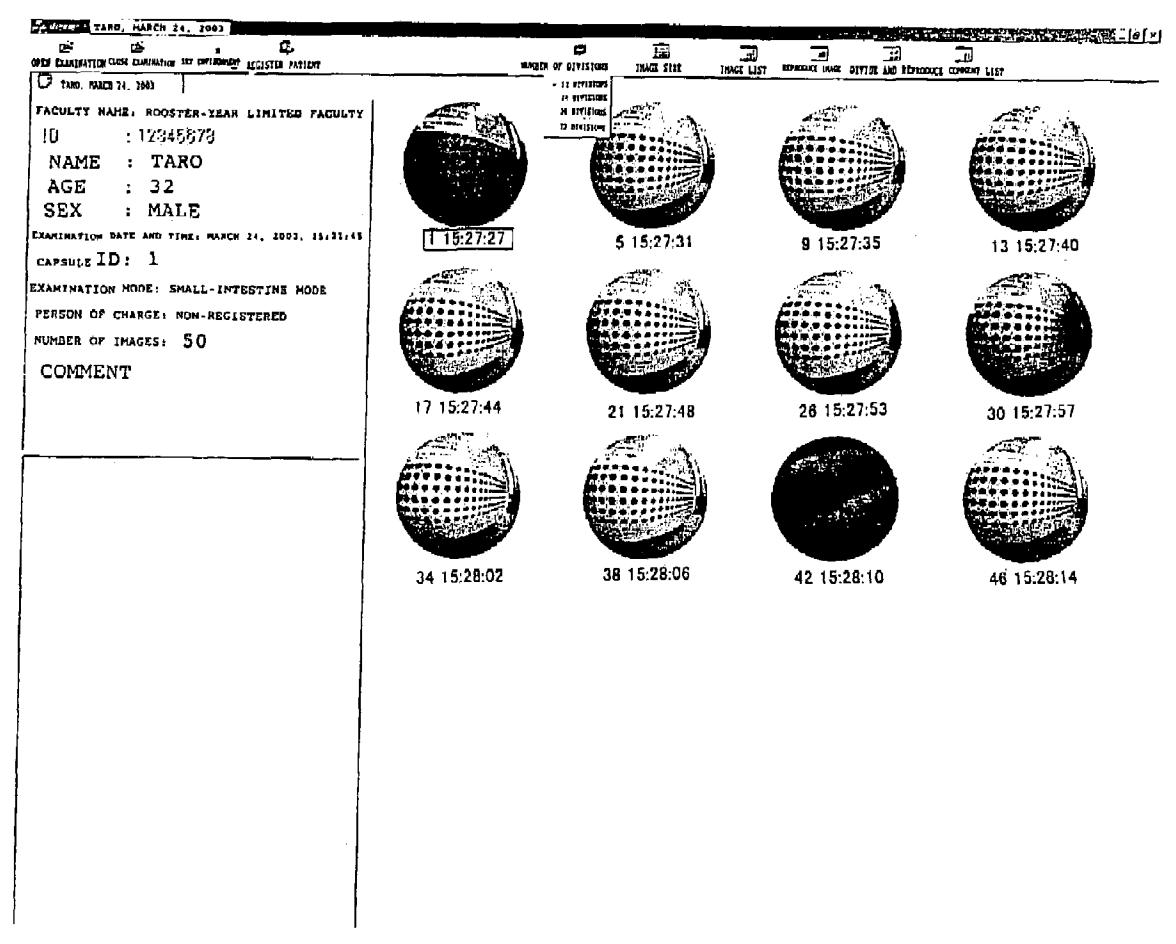

According to the first embodiment, referring to FIG. 7, it is possible to change and set the number of divided images displayed once on the display screen of the monitor. In the example of FIG. 7, the image is divided into 12 images and the interval of the number of divided images is changed by changing the number of divided images.

Therefore, the user selects the number of divisions, thereby displaying the images at the interval of the user's desired number of images.

In addition to the above-mentioned operation, the operation may be as follows according to a modification.

When the display device 5 is connected to the recording device 4, the recording device 4 may transmit the image data to the display device 5 without recording the image data in the PC card memory 45.

Figure 2:
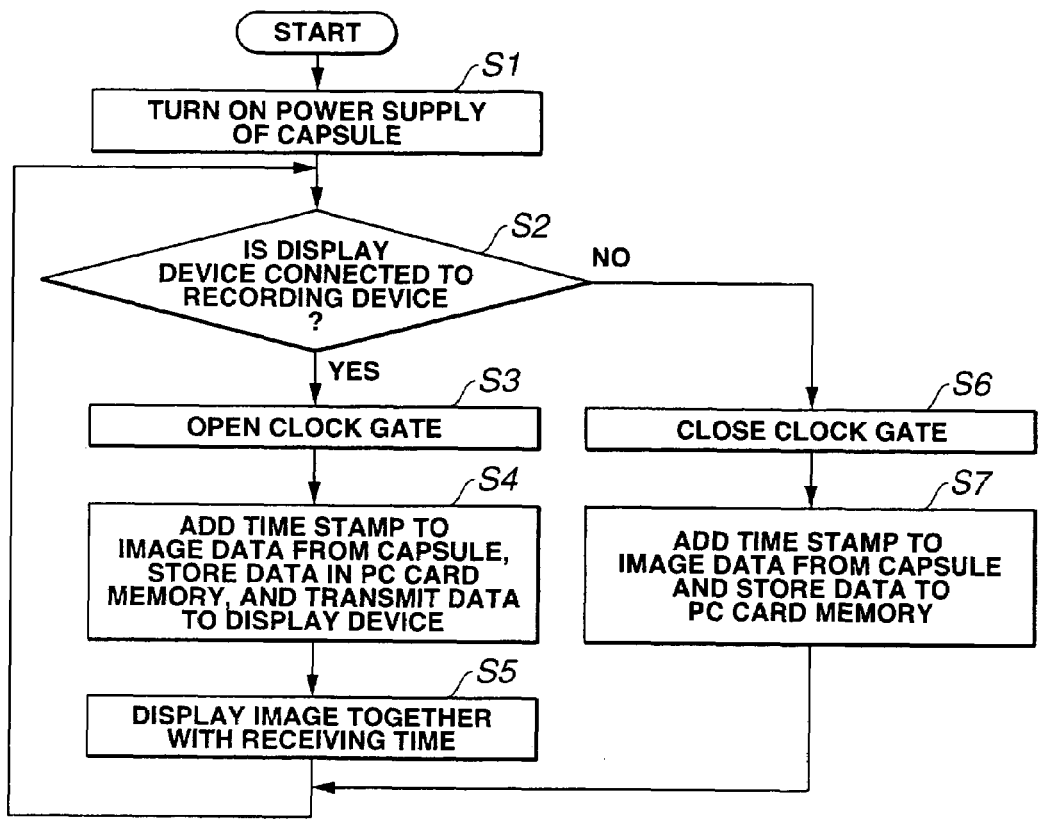

That is, in the flowchart showing the operation details shown in FIG. 2 according to the first embodiment, the time stamp is added to the image data from the capsule 3 and the processing details in step S4 are transmitted to the display device 5 together with the image data having the time stamp. The details may be changed to prevent the recording of the image data in the PC card memory 45.

Therefore, when the display device 5 is not connected to the recording device 4, the operation is the same as that according to the first embodiment. As mentioned above, the operating mode of the recording device 4 may be changed depending on the connection or disconnection of the display device 5 according to the modification.

When the display device 5 is connected to the recording device 4, a DC voltage for detecting the connection may be outputted to the voltage detecting circuit 49 from the display device 5 and the voltage may charge the battery 36a or 36b in the power supply block 25.

Figure 8:
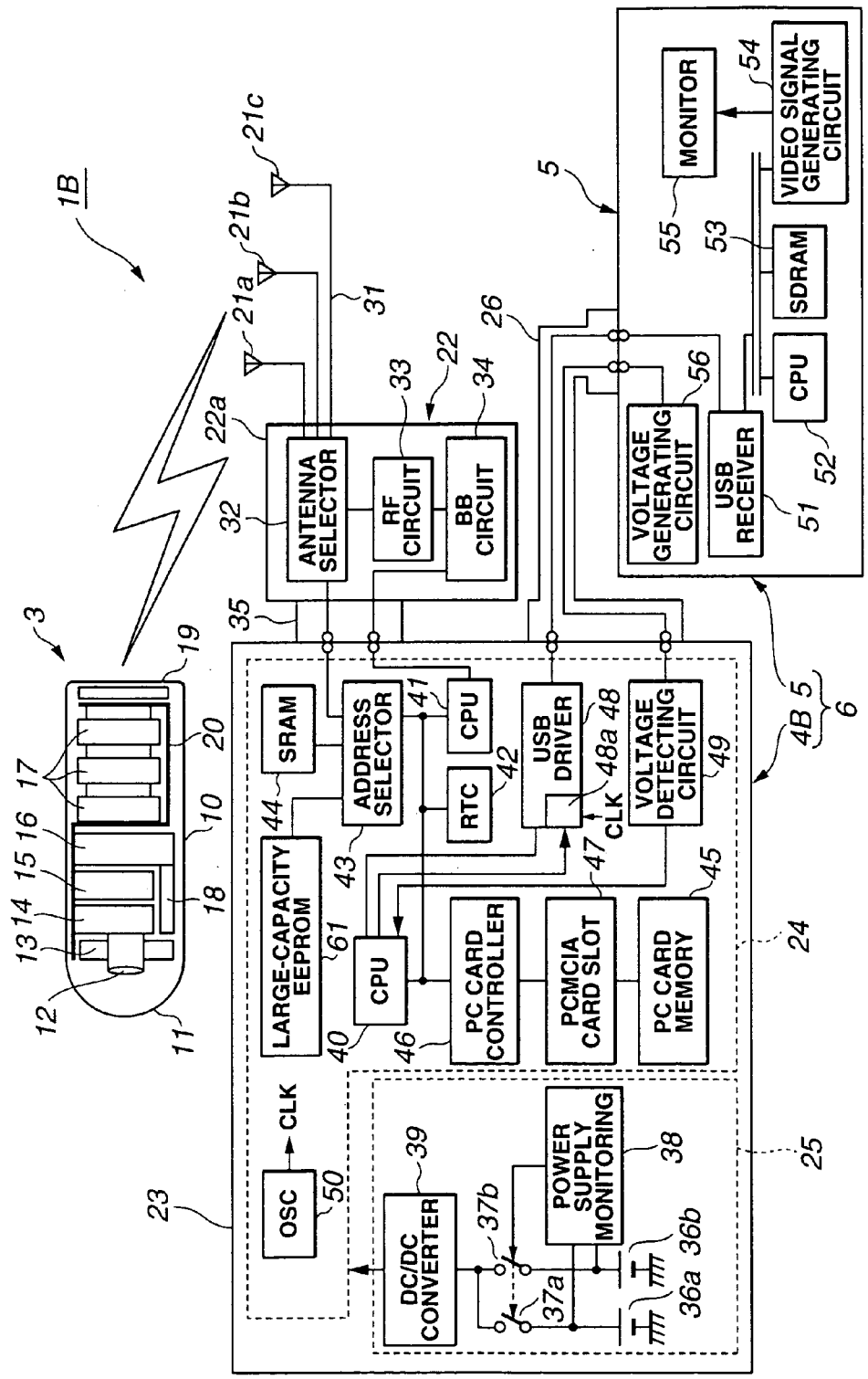
FIG. 8 is a diagram showing the structure of a capsular medical apparatus according to a second embodiment of the present invention.

FIG. 8 shows a second embodiment of the present invention.

Referring to FIG. 8, a capsular medical apparatus 1B according to the second embodiment comprises: the capsule 3; a recording device 4B; and the display device 5. The recording device 4B according to the second embodiment is formed by providing, for the recording device 4, a large capacity EEPROM 61 as a non-volatile memory which is electrically overwritten (with a large capacity). That is, according to the second embodiment, the recording device 4B comprises a plurality of pieces of information-recording means for selective use.

Further, according to the second embodiment, in the recording device 4B, the EEPROM 61 with the large capacity is connected via the address selector 43 to a bus to which the CPUs 41 and 42 and the RTC 42 are connected, similarly to the SRAM 44. The CPU 40 controls the operation that the received image data is stored in the large EEPROM 61 when the PC card memory 45 is not attached to the PCMCIA slot 47 in the recording device 4B.

The PC card memory 45 is attached to the recording device 4B. When the PC card memory 45 overflows due to the recording of the image data or the like, the CPU 40 successively controls the operation to write the data to the large EEPROM 61.

Other operations are the same as those according to the first embodiment.

According to the second embodiment, in addition to the advantages of the first embodiment, the image data picked-up by the capsule 3 is stored when the PC card memory 45 is not attached to the recording device 4B.

Figure 9:
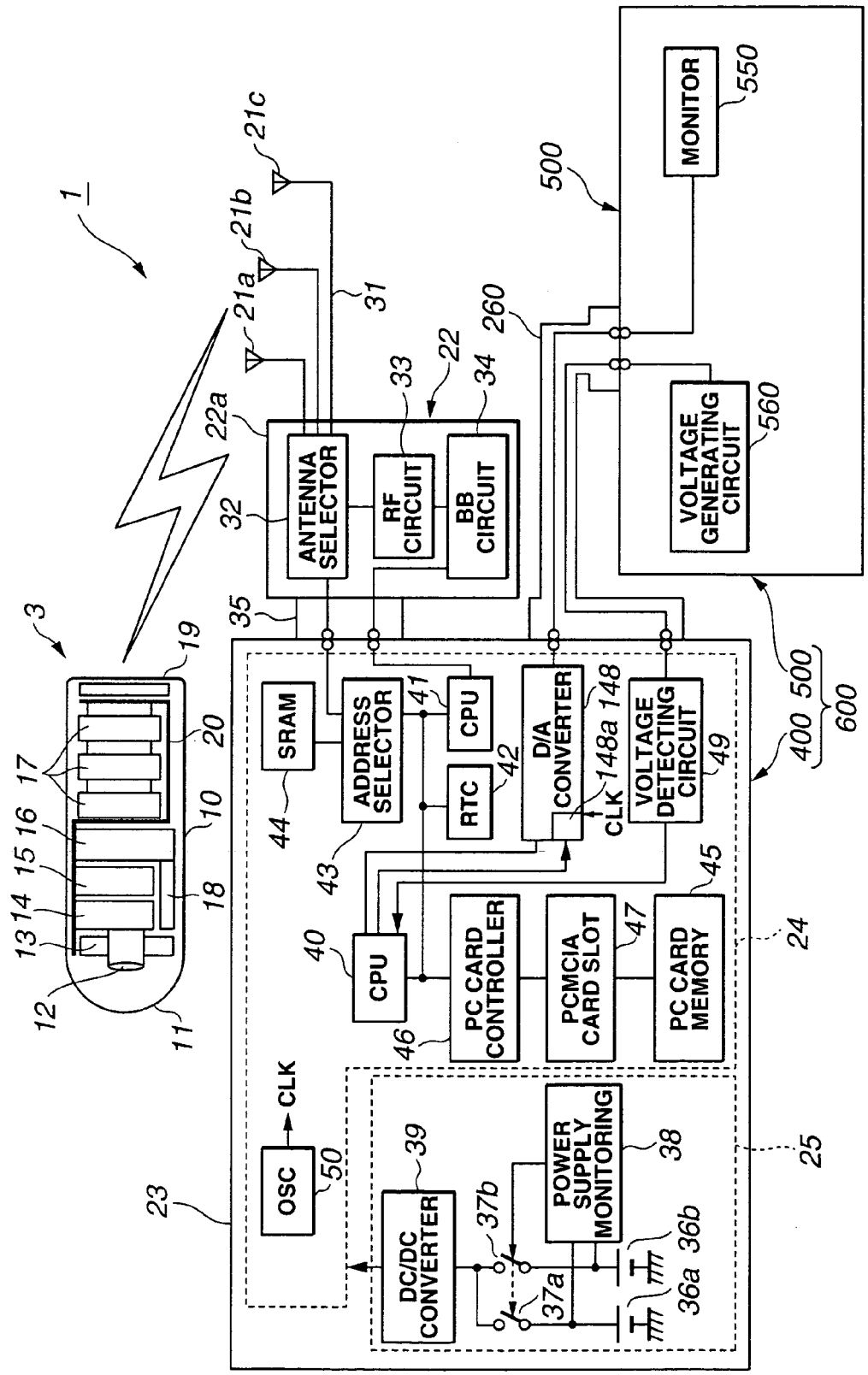
FIG. 9 is a diagram showing the structure of a capsule endoscope apparatus according to a third embodiment of the present invention.

FIG. 9 shows a third embodiment of the present invention.

According to the first embodiment, the recording device 4 is connected to the display device 5 by the USB cable 26. However, according to the third embodiment, data is communicated between a recording device 400 and a display device 500, which form an extracorporeal device 600, by using an analog video signal cable 260.

Therefore, in place of the USB driver 48 provided for the display device 5 according to the first embodiment, a D/A converter 148 is arranged to the recording device 400 and the living body information is transmitted to the display device 500 via the D/A converter 148. Reference numeral 148a denotes a clock gate.

The display device 500 directly displays the living body information on a monitor 550 because the recording device 400 transmits the living body information as an analog signal. Reference numeral 560 denotes a voltage generating circuit having the same function as that of the voltage generating circuit 56 according to the first embodiment.

According to the third embodiment, the recording device 400 transmits the living body information as the analog signal to the display device 500. Thus, the USB receiver 51 and the CPU 52 which are necessary according to the first embodiment are unnecessary and thus the structure of the display device 500 can be simplified.

As mentioned above, according to the present invention, the operation or the like is checked by connecting the display device upon starting the apparatus or the like. When the operation check or the like is unnecessary, the display device is detached and thus the load of the patient is reduced.

According to the above embodiments, the capsule 3 for picking up the optical image data is used. However, a capsule for obtaining ultrasonic image data can be used.

In addition to the acquisition of the image data, a capsule having a function for detecting pH or the like can be used and further a capsule for medical action such as medicine spray or the like can be used.

Having described the preferred embodiments of the invention referring to the accompanying drawings, it should be understood that the present invention is not limited to the those precise embodiments and various changes and modifications thereof could be made by one skilled in the art without departing from the spirit or scope of the invention as defined in the appended claims.

What is claimed is:

1. A capsular medical apparatus comprising:
   a capsule which can be swallowed or inserted in the body;
   a recording device which receives living body information transmitted from the capsule and which records the received information;
   a battery which supplies power to the recording device;
   a display device which displays the living body information;

a detecting unit which detects the connection between the recording device and the display device; and a transfer unit which transfers the living body information to the display device from the recording device substantially concurrently with the transmission of the living body information from the capsule to the recording device.

2. The capsular medical apparatus according to claim 1, wherein the recording device comprises a control unit which determines a signal from the detecting unit and which reduces consumption of the battery.

3. An examining method using a capsular medical apparatus having a capsule which can be swallowed or inserted in the body;

a recording device powered by a battery which receives living body information transmitted from the capsule and which records the received information; and a display device which displays the living body information, the examining method using the capsular medical apparatus, comprising:

a step of receiving the living body information transmitted from the capsule and recording the received information in the recording device;

a step of detecting the connection between the recording device and the display device independently of the connection; and a step of canceling a standby mode of a transfer unit upon detecting the connection and transferring the living body information transmitted from the capsule to the display device substantially concurrently with the transmission of the living body information from the capsule to the recording device.

4. A capsular medical apparatus comprising:

a capsule which can be swallowed or inserted in the body;

a recording device which receives living body information transmitted from the capsule and which records the received information;

a battery which supplies power to the recording device;

a display device to display the living body information substantially concurrently with the transmission of the living body information from the capsule to the recording device; and a detecting unit which detects the connection between the recording device and the display device;

wherein an operating mode of the recording device is changed in accordance with a detected result of the detecting unit.

5. The capsular medical apparatus according to claim 4, wherein the recording device records the received living body information in a recording unit therein when the detecting unit detects that the display device is not connected.

6. The capsular medical apparatus according to claim 4, wherein the recording device transmits the received living body information to the display device when the detecting unit detects that the display device is connected.

7. The capsular medical apparatus according to claim 4, wherein the recording device records the received living body information in a recording unit therein and transmits the received living body information to the display device when the detecting unit detects that the display device is connected.

8. The capsular medical apparatus according to claim 4, wherein the detecting unit detects the connection or disconnection by a voltage.

9. The capsular medical apparatus according to claim 4, wherein the living body information is image information.

10. The capsular medical apparatus according to claim 9, wherein the display device displays a plurality of pieces of image information.

11. The capsular medical apparatus according to claim 4, wherein the recording device adds date and time information for reception upon receiving the living body information.

12. The capsular medical apparatus according to claim 4, wherein the detecting unit sets, to a standby mode with low consumption-power, an operating state of a transfer unit which transfers the living body information to the display device from the recording device when the detecting unit detects that the display device is not connected.

13. A capsular medical apparatus comprising:

a capsule which can be swallowed or inserted in the body;

a recording device which receives living body information transmitted from the capsule;

a display device which displays the living body information;

a detecting unit which detects a connection between the recording device and the display device; and a battery which supplies power to the recording device;

wherein the recording device is equipped with following two operation modes;

(a) living body information receiving mode, wherein, an antenna is connected to the recording device to receive living body information transmitted from the capsule;

(b) living body information receiving and displaying mode, wherein an antenna is connected to the recording device to receive living body information transmitted from the capsule when the display device is connected to the recording device to substantially concurrently display the received living body information with the transmission of living body information from the capsule to the recording device.

14. A capsular medical apparatus according to claim 13, wherein the recording device reduces consumption current when operated in the operation mode (a).

15. A capsular medical apparatus according to claim 13, wherein the recording device is equipped with two non-volatile memories.

16. A capsular medical apparatus according to claim 15, wherein the two non-volatile memories has different storage capacity.

17. A capsular medical apparatus according to claim 15, wherein one of the two non-volatile memories are detachable from the recording device.

18. A capsular medical apparatus according to claim 17, wherein the recording device records the living body information to the two non-volatile memories in order of detachable non-volatile memory and the other non-volatile memory.

19. A capsular medical apparatus according to claim 13, wherein the display device is adapted to set a parameter of the recording device.

20. A capsular medical apparatus according to claim 13, wherein the display device is adapted to display plural of living body information enabling to open one of the plural living body information by clicking a tab.

21. A capsular medical apparatus according to claim 13, wherein the recording device records the received living body information when operated in mode (a).

22. A capsular medical apparatus according to claim 13, wherein the operation modes are switched based on the connection of the recording device and the display device.

23. A capsule medical apparatus comprising:

a capsule which can be swallowed or inserted in the body;

a recording device which receives living body information transmitted from the capsule and which records the received information;

a display device which displays the living body information and is formed independently from the recording device;

a battery which supplies power to the recording device;

a connecting unit which detachably connects the recording device and the display device;

a detecting unit which detects the connection between the recording device and the display device; and a transferring unit which transfers the living body information from the recording device to the display device, wherein the capsule medical apparatus includes a first operating mode in which the recording device transfers the living body information to the display device substantially concurrently with the transmission of the living body information from the capsule to the recording device, if detected result of the detecting unit shows that the connection is made, and a second operating mode in which the recording device records the living body information therein without transferring the living body information to the display device, if detected result of the detecting unit does not show that the connection is made.

* * * * *